(12) United States Patent
Yevmenenko et al.

(10) Patent No.: US 8,540,726 B2
(45) Date of Patent: Sep. 24, 2013

(54) HEADLESS COMPRESSION SCREW WITH INTEGRATED REDUCTION-COMPRESSION INSTRUMENT

(75) Inventors: Yan Yevmenenko, West Chester, PA (US); Walter Pistoia, Biel (CH); Andre Frenk, Brittnau (CH); Florian Beutter, Solothurn (CH); Franco Cicoira, Selzach (CH)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/527,162

(22) Filed: Jun. 19, 2012

(65) Prior Publication Data
US 2012/0283785 A1 Nov. 8, 2012

Related U.S. Application Data

(63) Continuation of application No. 11/205,829, filed on Aug. 16, 2005, now Pat. No. 8,216,243, which is a continuation-in-part of application No. 10/861,818, filed on Jun. 4, 2004, now Pat. No. 8,273,113, which is a continuation of application No. PCT/CH01/00698, filed on Dec. 4, 2001.

(51) Int. Cl.
*A61B 17/58* (2006.01)

(52) U.S. Cl.
USPC .......................................... 606/104; 606/304

(58) Field of Classification Search
USPC ......... 606/104, 300, 301, 304, 305, 310–312, 606/319, 323; 411/412, 413, 415
See application file for complete search history.

*Primary Examiner* — Mary Hoffman
*Assistant Examiner* — Tara Carter
(74) *Attorney, Agent, or Firm* — Fay Kaplun & Marcin, LLP

(57) ABSTRACT

A method is for implanting Bone Screw: screwing into a threaded bore in a distal portion of Implantation Instrument a rear threaded portion of Screw having a front threaded portion separated from the rear portion by an unthreaded middle portion, Screw including a central bore hole therethrough dimensioned to accommodate a guide wire; inserting the wire into a first target portion of bone; inserting Instrument over the wire such that the front threaded portion is adjacent to the first target portion; rotating Instrument to insert the front threaded portion into the first target portion while a locking component is engaged to prevent rotation of Screw relative to Instrument; and rotating Screw with the tool to drive Screw further into the first target portion to a desired depth and out of engagement with Instrument while the component is disengaged to permit rotation of Screw relative to Instrument.

13 Claims, 15 Drawing Sheets

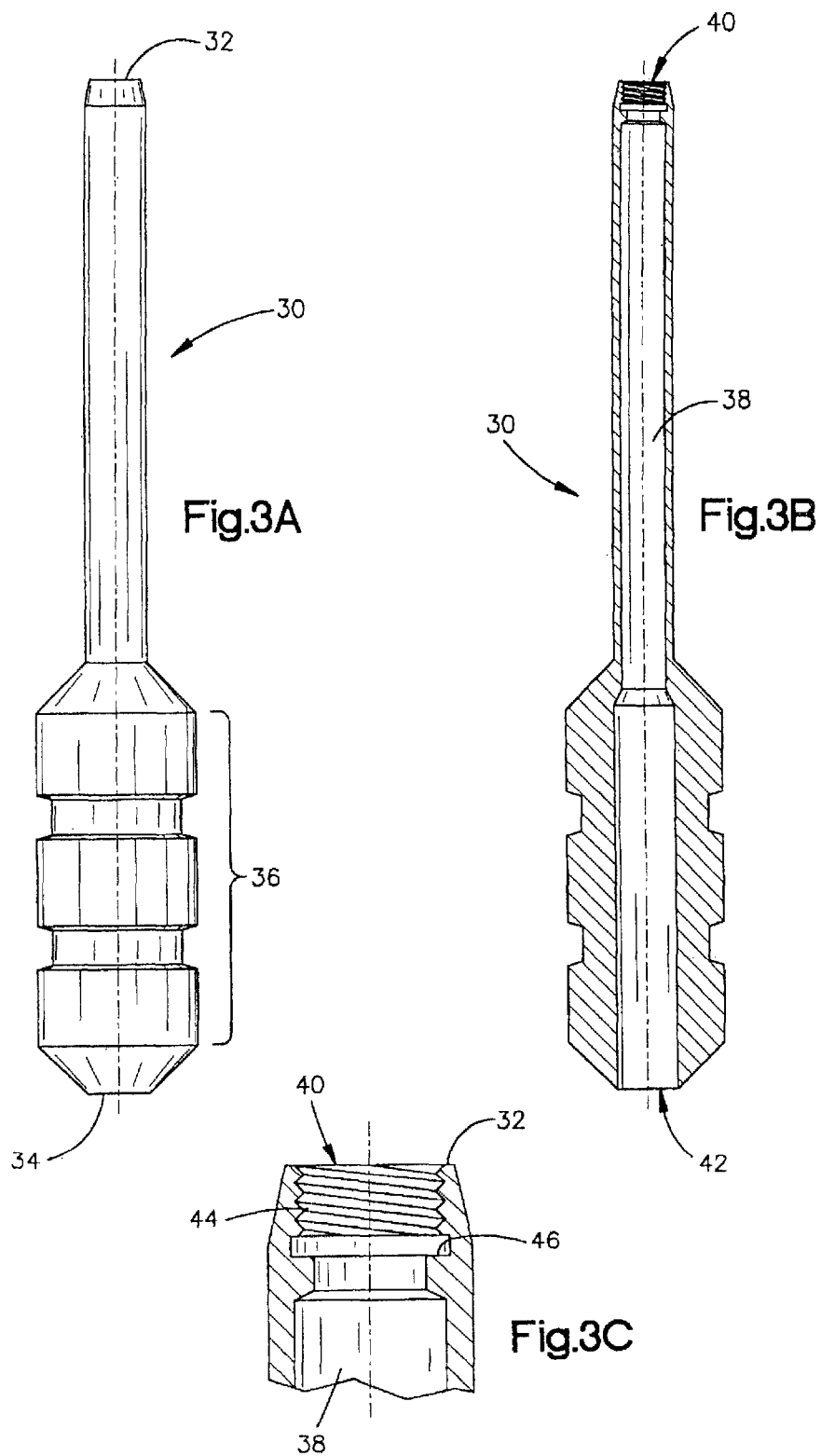

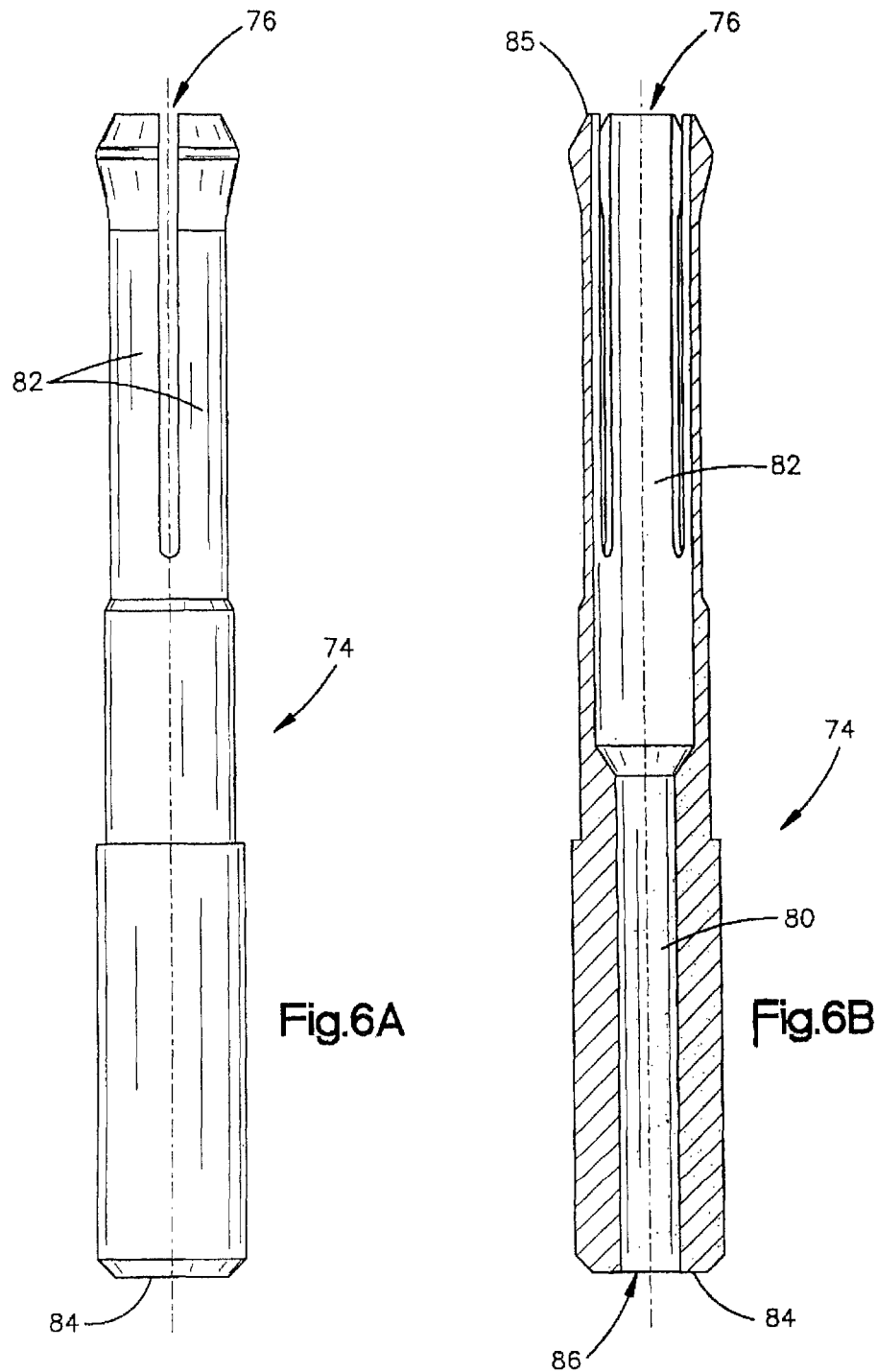

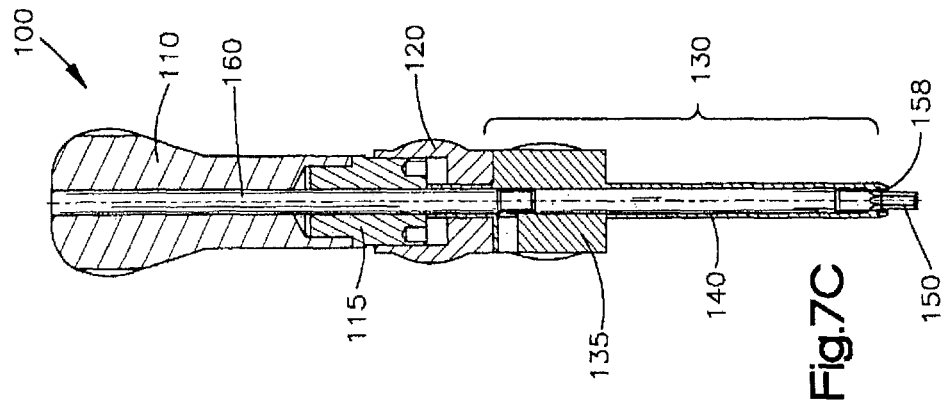
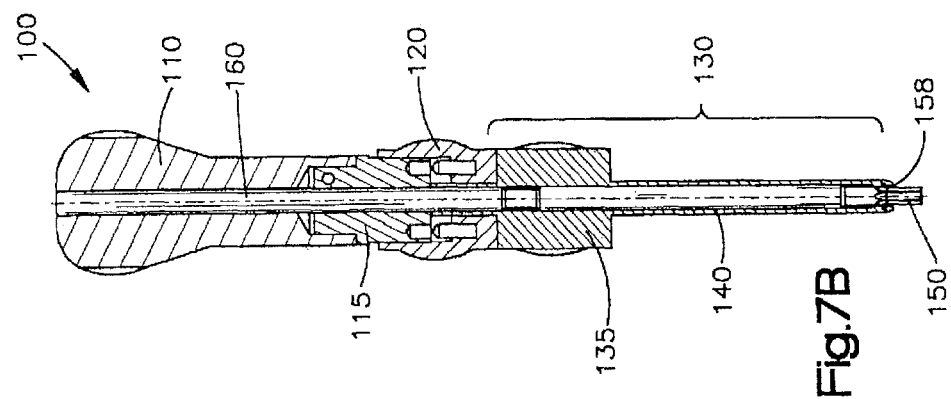
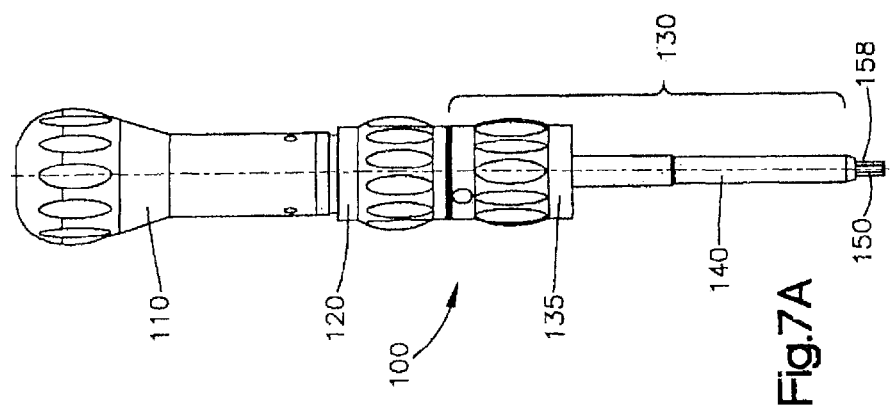

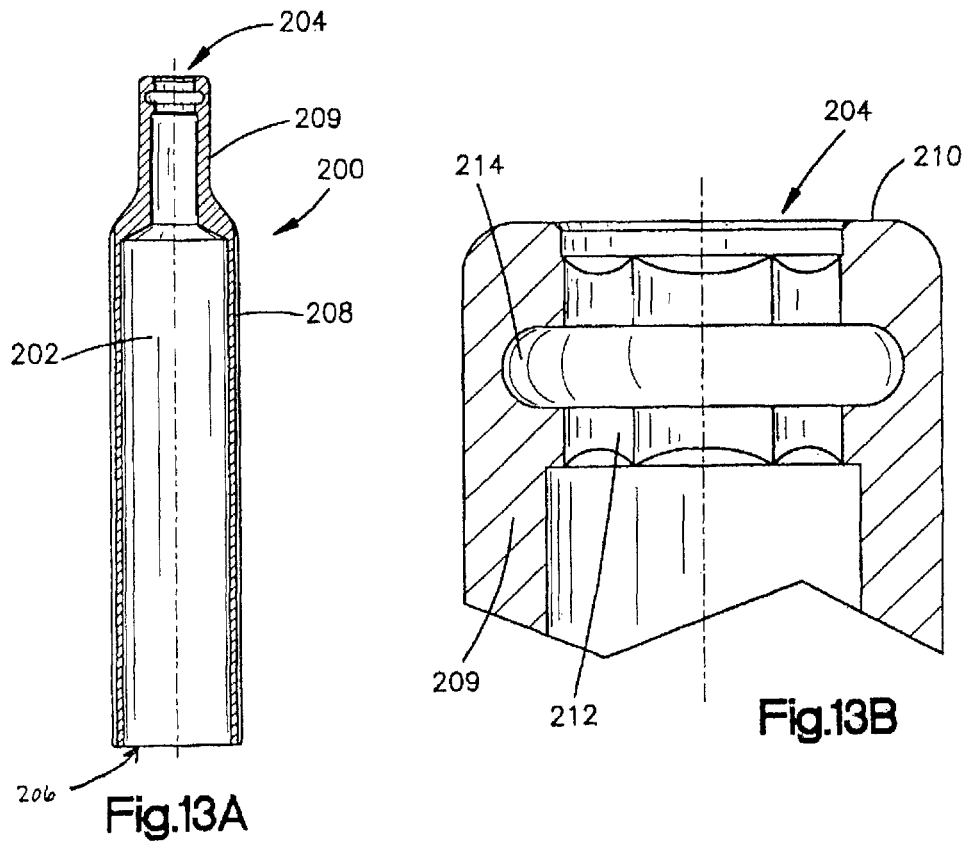
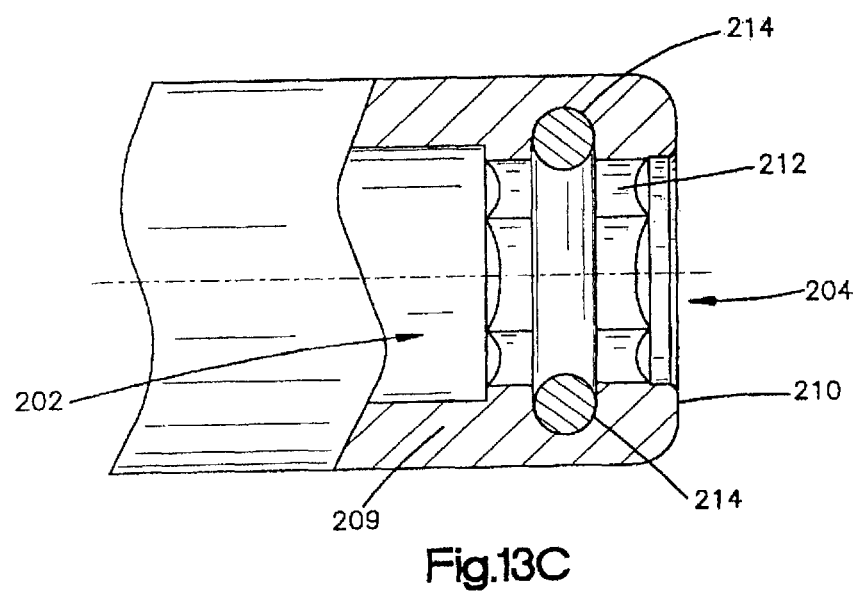

HEADLESS COMPRESSION SCREW WITH INTEGRATED REDUCTION-COMPRESSION INSTRUMENT

CROSS REFERENCE TO RELATED APPLICATION

The present application is a Continuation Application of U.S. patent application Ser. No. 11/205,829 filed on Aug. 16, 2005 entitled "Headless Compression Screw with Integrated Reduction-Compression Instrument", now U.S. Pat. No. 8,216,243, which is a Continuation-In-Part of U.S. patent application Ser. No. 10/861,818 filed on Jun. 4, 2004 which is Continuation of PCT Patent Application Serial No. PCT/CH2001/000698 filed on Dec. 4, 2001. The disclosures of the above applications/patents are incorporated herein by reference.

FIELD OF THE INVENTION

The invention relates to a bone screw for connecting two bone fragments, to a device for implanting such a bone screw, and to a method for setting, compressing and/or fixing bone fragments.

BACKGROUND OF THE INVENTION

Bone screws are used in various ways in osteosynthesis, for example, for setting bone fragments, as compression screws or for fixing bone fragments.

A bone screw with two axially terminal threaded segments and a middle threadless segment is known from U.S. Pat. No. 5,019,079 to Ross. The diameter of the middle segment corresponds essentially to the external diameter of the external thread at the distal threaded segment, but is larger than the core diameter of the external thread at the proximal threaded segment, so that the middle segment can be used for laterally stabilizing the two bone fragments of the fracture. It may be a disadvantage of this particular construction of bone screws that the two external threads have different pitches, so that the different steps for the implantation, the setting the bone fragments, the compression of the bone fragments and the recessing of the screw head cannot be carried out separately from one another.

SUMMARY OF THE INVENTION

Pursuant to the invention, this objective is accomplished with a bone screw, and with a device for implanting such a bone screw, as well as with a method for setting, compressing and/or fixing bone fragments.

The inventive bone screw comprises essentially two threaded segments, which are disposed coaxially with the longitudinal axis and terminally at the bone screw, the pitches $S_V$ and $S_H$ of the front and rear segments respectively, which may be identical or may be different from one another. After these two bone fragments have been set and compressed, wherein only the front threaded segment is screwed into the distal bone fragment while the rear threaded segment is screwed, for example, into an implantation instrument and not yet into the proximal bone fragment, the bone screw can be screwed further into the bone fragments, until the rear threaded segment also is recessed completely in the proximal bone fragment. This can be accomplished without at the same time changing the position of the bone fragments relative to one another and without changing the compression of the two bone fragments. The two threaded segments are constructed so that the external diameter of the front threaded segment is smaller than or equal to the core diameter of the external thread at the rear threaded segment.

An advantage of the inventive bone screw and the inventive device are that due to the pitch of the external thread at the front threaded segment and at the rear threaded segment being the same, the steps of setting the bone fragments, compressing the bone fragments, and recessing the head of the screw can be carried out separately and in a controlled manner.

Because the rear threaded segment is configured with a core diameter, which may be larger than or equal to the external diameter of the front threaded segment, interaction of the rear threaded segment with the thread already cut in the bone fragments for the front threaded segment can be avoided.

Preferably, the external threads at the front and rear threaded segments are self-cutting threads.

A preferred embodiment of the inventive bone screw includes, between the two threaded segments, a middle, threadless segment, which has an external diameter, which is smaller than or equal to the core diameter of the external thread at the front threaded segment. With that, the front threaded segment can be screwed completely into the distal bone fragment and the borehole in the proximal bone fragment does not have to be enlarged relative to the borehole in the distal bone fragment for setting and compressing the bone fragments. Compared to embodiments of known bone screws, the front threaded segment of which directly adjoins the rear threaded segment in the axial direction and for which the borehole in the proximal bone fragment would have to be enlarged so that the front threaded segment can be screwed only into the distal bone fragment, a higher stability of the connection between the bone screw and the proximal bone fragment can furthermore be attained with the present device.

The inventive device serves for setting, compressing and fixing bone fragments by means of a bone screw and includes a surgical implantation instrument, which has a central borehole through which a screwdriver can be passed, extending coaxially through the implantation instrument. Furthermore, the central borehole is expanded from the front end of the implantation instrument up to a depth T, so that a shoulder is formed at the depth T. In the expanded part of the central borehole, there is an internal thread, which is complementary to the external thread of the rear threaded segment of the bone screw, so that the rear threaded segment of the bone screw can be screwed into the central borehole up to a depth T. The depth T is selected so that T may be greater than L, where L is the length of the rear threaded segment of the bone screw. With that, it can be achieved that the rear threaded segment of the bone screw can be screwed completely into the central borehole of the implantation instrument. However, T may also be equal to or less than L, which may have the effect of partially inserting the rear threaded segment of the bone screw into the central borehole.

BRIEF DESCRIPTION OF THE DRAWINGS

The invention and further developments of the invention are explained in even greater detail in the following by means of the partially diagrammatic representations of several examples. In the drawings.

FIG. 3A shows a side view of an embodiment of a compression sleeve;

FIG. 3B shows a cross-sectional view of the compression sleeve of FIG. 3A;

FIG. 3C shows an enlarged partial cross-sectional view of the compression sleeve of FIGS. 3A-3B;

FIG. 6A shows a side view of a coupling member for use with the protection handle of FIGS. 5A-5B;

FIG. 6B shows a cross-sectional view of the coupling member of FIG. 6A;

FIG. 7A show a side view of an embodiment of a combi-instrument;

FIGS. 7B-7C show cross-sectional views of the combi-instrument of FIG. 7A;

FIG. 13A shows a side view of an embodiment of a compression sleeve having a hex-shaped inlet for use with a plastic-sealed screw;

FIG. 13B shows an enlarged side view of the compression sleeve of FIG. 13A;

FIG. 13C shows an enlarged partial cross-sectional view of the compression sleeve of FIG. 13A;

DETAILED DESCRIPTION OF THE INVENTION

Figure 1:
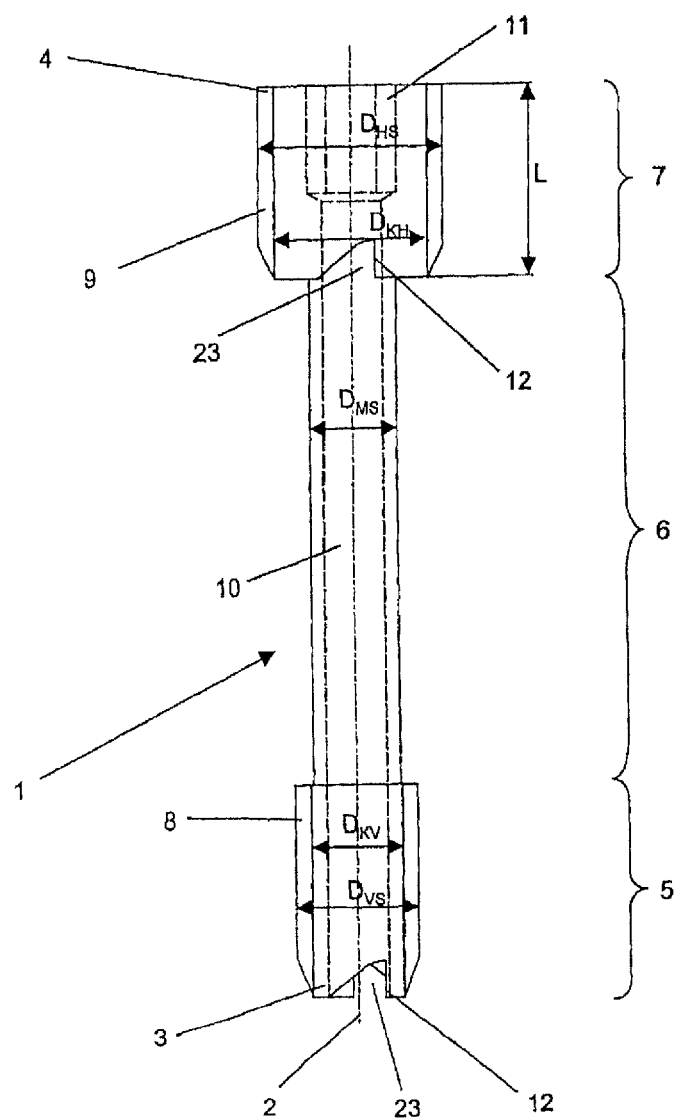
FIG. 1 shows a cross-sectional view of an embodiment of the inventive bone screw.

A preferred embodiment of the inventive bone screw 1 is shown in FIG. 1. This bone screw 1 includes a rear threaded segment 7 with an external thread 9, which has a core diameter $D_{KH}$, an external diameter $D_{HS}$ and a pitch $S_H$, a middle, threadless segment 6 with an external diameter $D_{MS}$, which adjoins the rear threaded segment 7 coaxially with the longitudinal axis 2, and a front threaded segment 5 with an external thread 8, which has a core diameter $D_{KV}$, an external diameter $D_{VS}$ and a pitch $S_V$. The two threaded segments 5, 7 have different diameters, that is, the core diameter $D_{KH}$ of the rear threaded segment 7 is larger than or equal to the external diameter $D_{VS}$ of the front threaded segment 5. The pitches of the two external threads 8, 9 may be identical, or may be different from one another. Moreover, the lead of the front threaded segment 5 may be equal to or different from the lead of the rear threaded segment 7. The external diameter $D_{MS}$ of the middle segment 6 is smaller than or equal to the core diameter $D_{KV}$ of the front threaded segment 5. Moreover, at the front end 3 of the bone screw 1 and at the transition between the rear threaded segment 7 and the middle segment 6, several indentations 23, distributed over the periphery of the two threaded segments 5, 7 which may be aligned axially, are disposed with cutting edges 12 essentially parallel to the longitudinal axis 2, so that these two external threads 8, 9 are constructed as self-cutting threads. At the rear end of 4 of the bone screw 1, means 11 for accommodating a screwdriver, for example, a hexagonal recess, Torx® or Phillips, are disposed coaxially. Moreover, the bone screw 1 is equipped with a central borehole 10, which extends from the front end 3 up to the rear end 4 and serves; for example, for accommodating a guiding wire (not shown).

Figure 2:
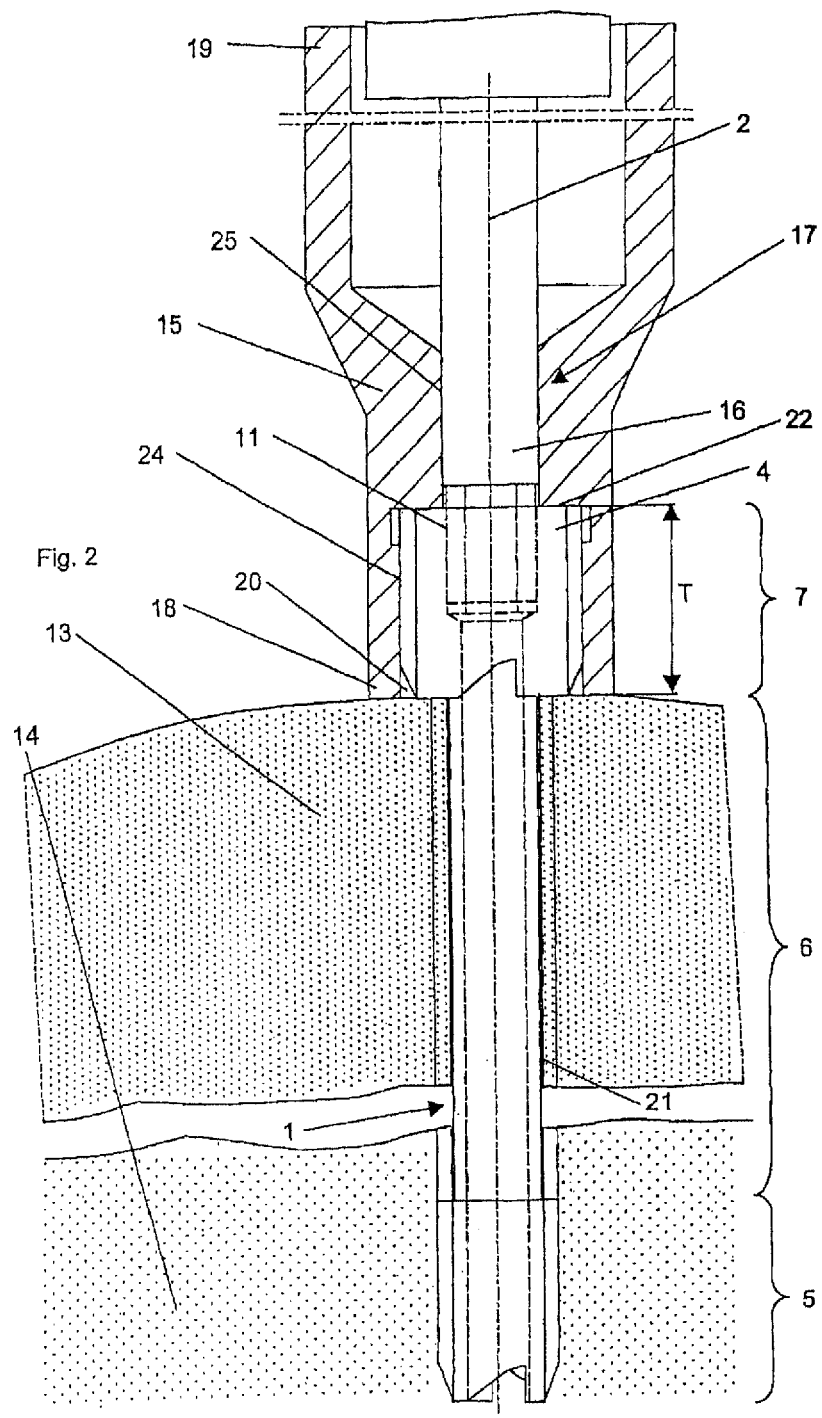
FIG. 2 shows a cross-sectional view of the embodiment shown in FIG. 1, an implantation instrument, and a screwdriver.

In FIG. 2, the inventive device is shown together with a bone screw 1, a portion of the rear threaded segment 7 is screwed into the implantation instrument 15 and the front threaded segment 5 of which is screwed completely into the distal bone fragment 14. The implantation instrument 15 includes a continuous central borehole 17, which is expanded from the front end 18 up to a depth T and, in expanded part 24, has an internal thread 20, which is complementary to the external thread 9. At the depth T, between the expanded part 24 of the central borehole 17 and the narrower part 25 of the central borehole 17, there is a shoulder 22, against which the rear end 4 of the bone screw 1 rests when the rear threaded segment 7 is screwed completely into the implantation instrument 15. A screwdriver 16 can be passed through the narrower part 25 of the central borehole 17 from the rear end 19 of the implantation instrument 15, so that the screwdriver 16 can be introduced into the means 11, which are disposed at the rear end 4 of the bone screw 1 for accommodating a screwdriver and the bone screw 1 can be rotated by means of the screwdriver 16 relative to the implantation instrument 15.

For setting, compressing and fixing the two bone fragments 13, 14, a borehole 21, passing through the proximal bone fragments 13 and into the distal bone fragment 14, may be produced. The diameter of the borehole 21 corresponds to the core diameter $D_{KV}$ (FIG. 1) of the external thread 8 at the front threaded segment 5 of the bone screw 1. Borehole 21 may be optional, however, particularly when bone screw 1 is self-drilling.

At the start of the implantation process, the rear, threaded segment 7 of the bone screw 1 is screwed completely and up to a depth T in the internal thread 20 into the central borehole of the implantation instrument 15. By rotating the implantation instrument 15 about the longitudinal axis 2, the bone screw may then screwed into the pre-drilled boreholes 21 in the two bone fragments 13, 14. Since the rear threaded segment 7 of the bone screw 1 is taken up completely in the implantation instrument 15, the external thread 9 of the rear threaded segment 7 cannot engage the proximal bone fragments 13, so that, as the implantation instrument 15 is rotated, only the front threaded segment 5 of the bone screw 1 can be screwed into the distal bone fragment 14. In this phase, the front end 18 of the implantation instrument 15 assumes the task of a screw head, so that, after the bone screw 1 has been brought into the two bone fragments 13, 14 far enough that the front end 18 of the implantation instrument 15 lies against the proximal bone fragment 14, the two bone fragments 13, 14 are moved towards one another by rotating the implantation instrument 15 further. As soon as the two bone fragments 13, 14 are in contact with one another, compression of the two bone fragments 13, 14 commences. As soon as the desired compression of the two bone fragments 13, 14 has been reached by rotating the implantation instrument 15 further, the screwdriver 16 is inserted through the central borehole 17 in the implantation instrument 15 into the means 11 for accommodating the screwdriver and the bone screw 1 is rotated further with the screwdriver 16, so that, while the implantation instrument 15 is held in place, the bone screw 1 is screwed out of the internal thread 20 at the front end 18 of the implantation instrument 15 and the rear threaded segment 7 is screwed into the proximal bone fragment 13, until the rear threaded segment 7 is brought completely beneath the surface of the proximal bone fragment 13. Since the two bone fragments 13, 14 are not moved relative to one another during this last process, the compression may be unchanged after the rear, threaded segment 7 is driven into the proximal bone fragment 13.

Preferably, the bone screw 1 is used where a screw head would interfere, for example, for fractures in the vicinity of a joint, for intraarticular fixation such as scaphoid fractures, for small fragments and for fixations in the vicinity of sinews, nerves and vessels. Bone screw 1 may also be used in conjunction with or adjacent to a bone plate (not shown).

FIGS. 3A-3C show an embodiment of a compression sleeve 30 for use with a bone screw 1. As seen in the side view of FIG. 3A, compression sleeve 30 may have a leading end 32, a trailing end 34, and a gripping portion 36 disposed near the trailing end 34. As seen in the cross-sectional view of FIG. 3B, compression sleeve 30 may have a bore 38 running through the sleeve 30, and extending between leading opening 40 and trailing opening 42. An enlarged view of the leading end 32 of the compression sleeve 30 is seen in FIG. 3C. Internal threads 44 may be disposed at and/or near the leading end 32 and leading opening 40 of the sleeve 30. Sleeve 30 may also have a shoulder 46 disposed adjacent internal threads 40. Shoulder 46 may be sized to prevent a bone screw 1 from protruding too far into the bore 38 of sleeve 30. Shoulder 46 may be positioned within bore 38 such that the rear threaded segment 7 of bone screw 1 can fully engage the internal threads 40. Compression sleeve 30 may be used in a substantially similar manner as implantation instrument 15, discussed supra.

Figure 4A:
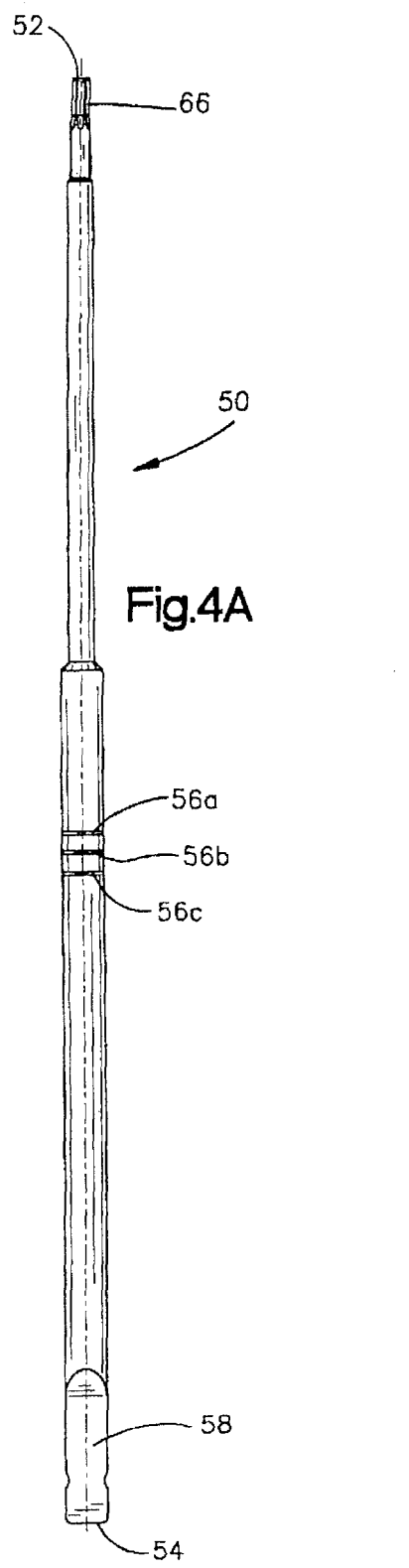
FIG. 4A shows a side view of an embodiment of a cannulated screwdriver.
Figure 4B:
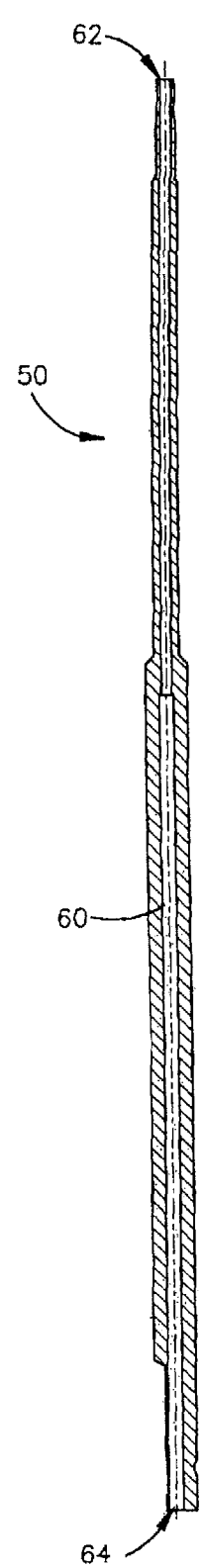
FIG. 4B shows a cross-sectional view of the screwdriver of FIG. 4A.

FIGS. 4A-4B show an embodiment of a screwdriver 50 for use with a bone screw 1. As seen in the side view of FIG. 4A, screwdriver 50 may have an engaging end 52, a trailing end 54, and indicia 56a, 56b, 56c. Screwdriver 50 may also have a depressed section 58 at or near the trailing end 54, which may aid in engaging a handle. As seen in the cross-sectional view of FIG. 4B, screwdriver 50 may have a bore 60 running between a leading opening 62 and a trailing opening 64. Screwdriver may also have an engaging portion 66 for engaging a bone screw 1 in a similar manner to that described supra in relation to screwdriver 16. Engaging portion 66 may be of any chosen shape to effectively engage a bone screw 1.

Indicia 56a, 56b, 56c may aid in determining the depth of insertion of a bone screw 1 in a bone or tissue. When inserted into a compression sleeve or other implantation instrument, indicia 56a, 56b, 56c may be fully or partially visible during use. As the engaging portion 66 of the screwdriver 50 engages a receiving portion (an embodiment of which is shown as means 11 above) of a bone screw 1, the bone screw 1 is further inserted in a bone or tissue, and may become disengaged with the internal threads 40 of a compression sleeve 30. As the screwdriver 50 is inserted farther into the bore 38 of sleeve 30, the indicia 56a, 56b, 56c may progressively become covered, such that as indicia 56c becomes covered by sleeve 30, the bone screw 1 may be fully inserted into a bone or tissue.

Figure 5A:
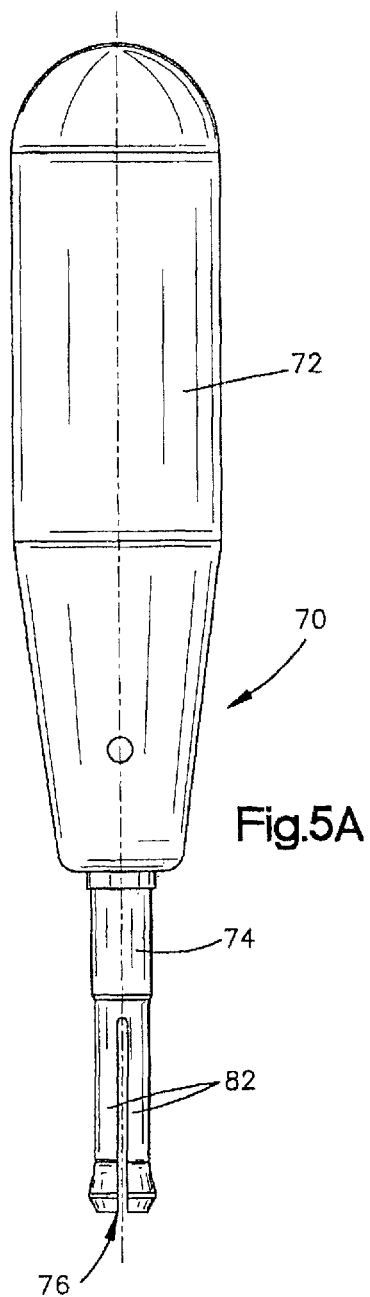
FIG. 5A shows a side view of an embodiment of a protection handle.
Figure 5B:
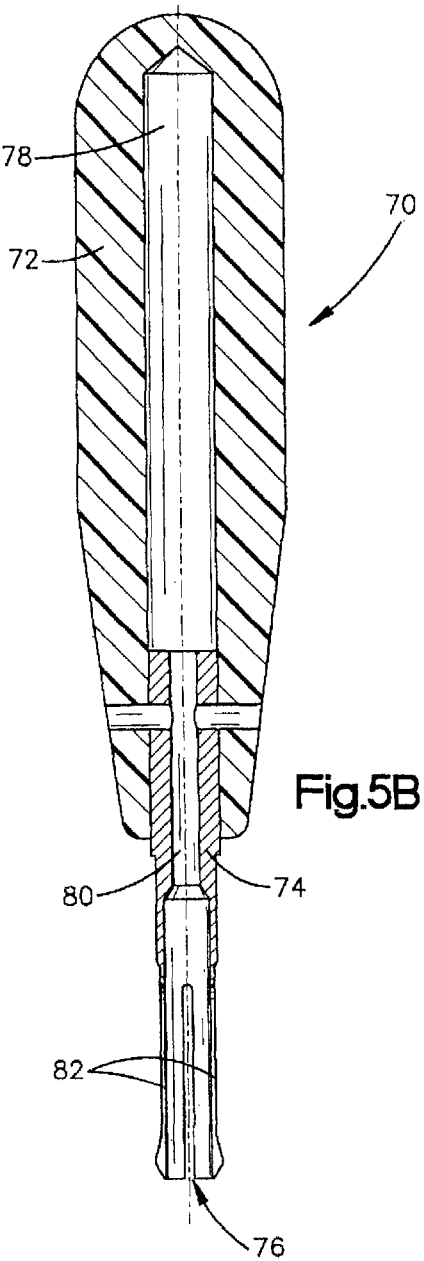
FIG. 5B shows a cross-sectional view of the protection handle of FIG. 5A.

FIGS. 5A-5B show an embodiment of a handle 70 for use with an instrument described herein. As seen in the side view of FIG. 5A, handle 70 may have a gripping portion 72, and a coupling member 74 having an leading opening 76 and expandable fingers 82. Coupling member 74 may be a separate and distinct component (as shown in FIGS. 6A-6B), and may be at least partially inserted into a compression sleeve 30 via opening 42. Expandable fingers 82 may be beneficial to resiliently contract within bore 38 of compression 30 to create a more secure fit. As seen in the cross-sectional view of FIG. 5B, handle 70 may also have a bore 78 for receiving coupling member 74. Receiving portion 74 may also have a bore 80 for receiving a portion of a guide wire (not shown) therethrough.

FIGS. 6A-6B show an embodiment of a coupling member 74 in more detail. As seen in the side view of FIG. 6A and cross-sectional view of FIG. 6B, coupling member 74 may have leading opening 76, a trailing opening 86, with a bore 80 extending therebetween. Coupling member 74 may also have a leading end 85 and a trailing end 86. Bore 80 may be sized and dimensioned to fit a guide wire (not shown).

In use, handle 70 may be beneficial to provide a safe and ergonomic way for a user to insert bone screw 1 into a bone segment. First, a guide wire may be inserted into a bone segment at a desired location. The compression sleeve 30, with bone screw 1 already engaged with internal threads 40, may be engaged with handle 70, and thereafter inserted over the guide wire, such that the front end 3 of the bone screw 1 is adjacent the bone surface. In this arrangement, the coupling portion 74 engages the compression sleeve 30 via its trailing opening 42, and the free end of the guide wire is housed in the bore 78 of handle 70. Bone screw 1 may then be inserted into the bone surface with the exposed, free end of the guide wire safely housed in the handle. After the bone screw 1 is inserted into the bone surface to a desired depth, the handle 70 and coupling portion 74 may be disengaged from the compression sleeve 30, and the screwdriver 50 may be brought into engagement to further insert the bone screw 1 into the bone surface and/or disengage the bone screw 1 from the compression sleeve 30. Thus, the configuration and removable engagement of handle 70 with compression sleeve 30 offers protection to the user from the free end of the guide wire, and also provides an ergonomic method to insert bone screw 1 at least partially into a bone surface.

FIGS. 7A-7C show an embodiment of another type of instrument, combi-instrument 100, that may be used with a bone screw 1. As seen in the side view of FIG. 7A, and cross-sectional views of FIGS. 7B-7C, combi-instrument 100 may have a handle 110, a locking collar 115, a locking ring 120, a compression sleeve 130 having a gripping portion 135 and a shaft portion 140, a screwdriver 150 having a leading portion 158, and a bore 160 extending therethrough.

In use, combi-instrument 100 may function in a substantially similar manner to that of the other devices described herein. One difference between the combi-instrument 100 and other devices described herein is that combi-instrument 100 may have a selective engagement feature that allows a bone screw 1 to be at least partially inserted with and without the use of screwdriver 150. As described in more detail below, the selective locking arrangement between locking collar 115 and locking ring 120 may selectively determine whether the compression sleeve 130 is fixed in relation to the handle 110 and screwdriver 150. As bore 160 may pass all the way through the combi-instrument 100, a guidewire (not shown) may be utilized for more precise and accurate placement and use of the instrument 100.

Figures 8A, 8B:
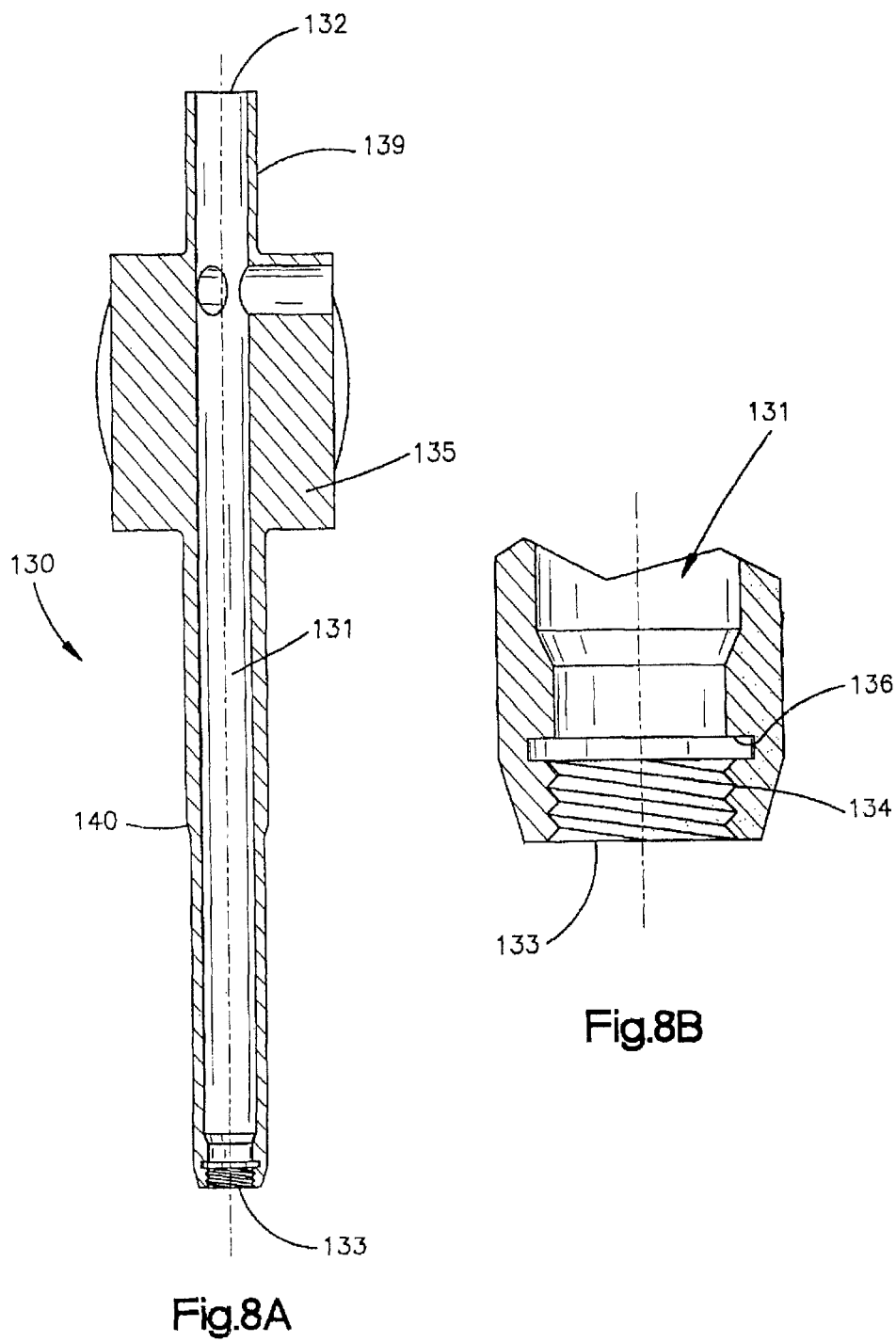
FIG. 8A shows a cross-sectional view of a compression sleeve for use with the combi-instrument of FIG. 7A.
FIG. 8B shows an enlarged cross-sectional view of the compression sleeve of FIG. 8A.

FIGS. 8A-8B show an embodiment of a compression sleeve 130 for use with combi-instrument 100. Compression sleeve 130 may be substantially similar in design and function to compression sleeve 30 and implantation instrument 15 described supra. Compression sleeve 130 may have a bore 131 extending between a leading opening 133 and a trailing opening 132. Sleeve 130 may also have a gripping portion 135 and a shaft 140. As with compression sleeve 30 discussed above, sleeve 130 may also have internal threads 134 for engaging a bone screw 1, and a shoulder 136 for restricting movement of a bone screw 1 within bore 131. Compression sleeve 130 also may have an auxiliary shaft portion 139, which is either polygonal or otherwise non-circular in shape, for receiving a locking ring 120 such that when locking ring 120 is received on the auxiliary shaft, the locking ring 120 cannot rotate relative to the compression sleeve 130. As such, compression sleeve 130 and locking ring 120 are rotationally fixed during use, although locking ring 120 may be slidably associated with the auxiliary shaft portion 139.

Figure 9A:
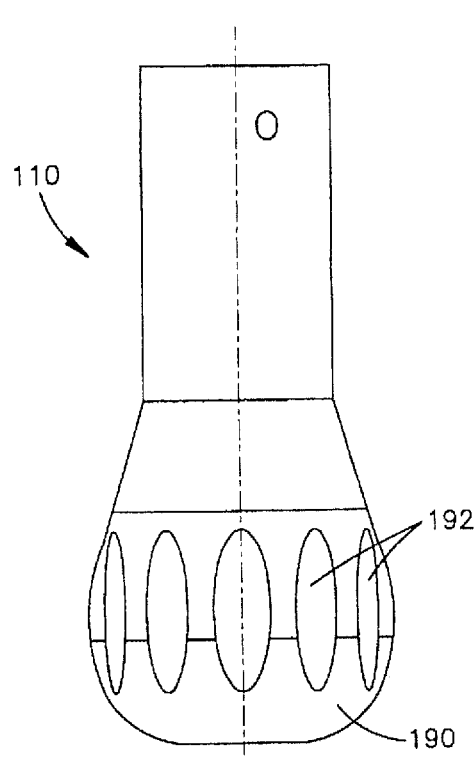
FIG. 9A shows a side view of a handle for use with the combi-instrument of FIG. 7A.
Figure 9B:
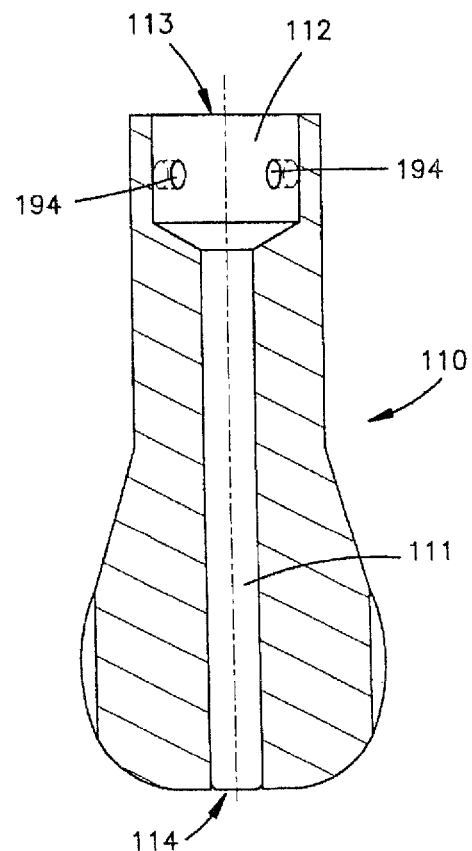
FIG. 9B shows a cross-sectional view of the handle of FIG. 9A.

FIGS. 9A-9B show an embodiment of a handle 110 for use with combi-instrument 100. Handle 110 may have a bore 111 extending between a leading opening 113 and a trailing opening 114. Handle 110 may also have a gripping portion 190, with indentations 192 for enhancing a user's gripping abilities. Handle 110 may further have an enlarged chamber 112, at least partially concurrent with bore 114, that may receive at least a portion of a locking collar 115. Handle 110 preferably is fixedly attached to locking collar 115 by way of fasteners (not shown) inserted into fixation holes 194.

Figures 10A, 10B:
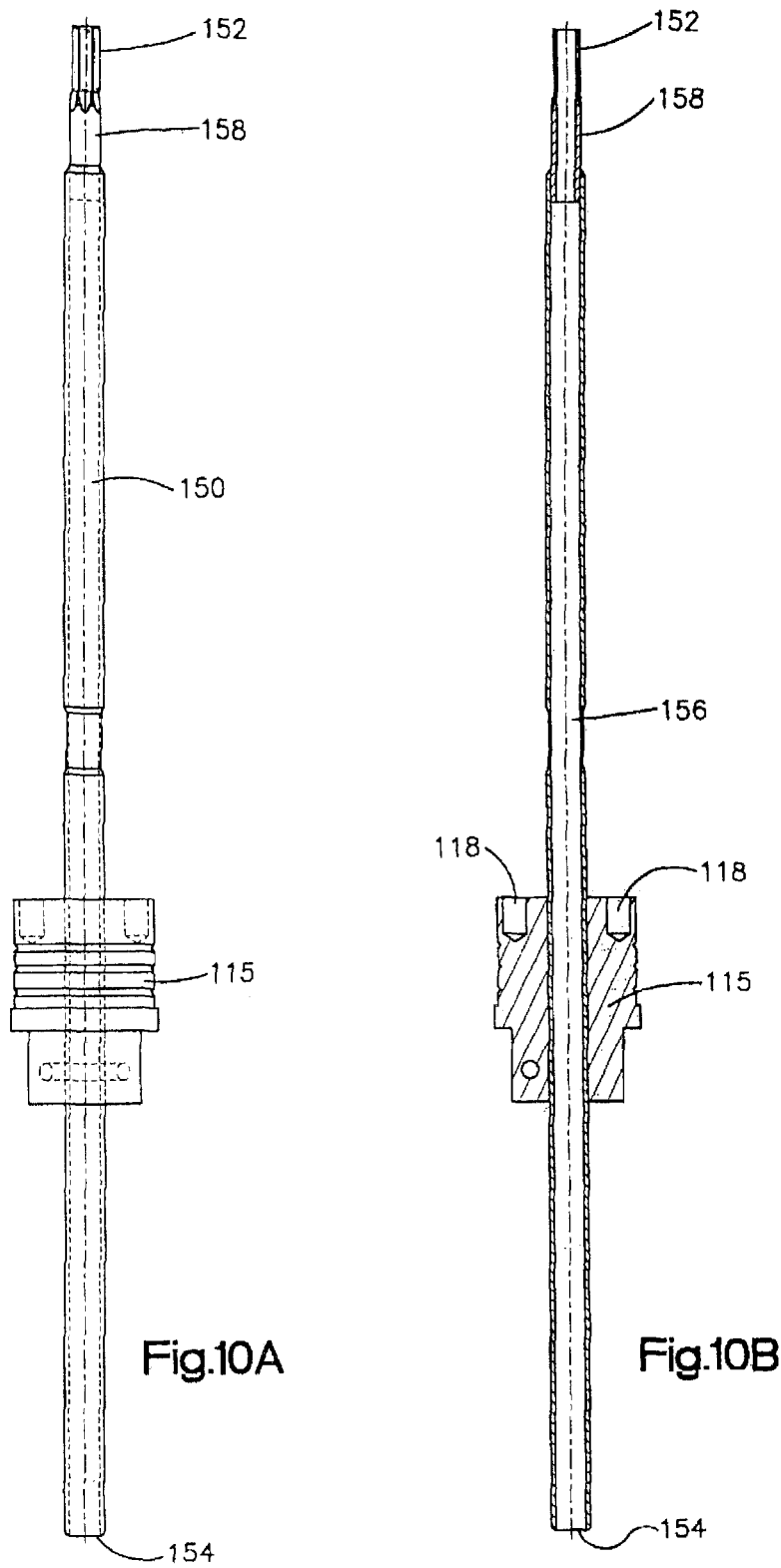
FIG. 10A shows a side view of a cannulated screwdriver and locking collar for use with the combi-instrument of FIG. 7A.
FIG. 10B shows a cross-sectional view of the cannulated screwdriver and locking collar of FIG. 10A.
Figure 10C:
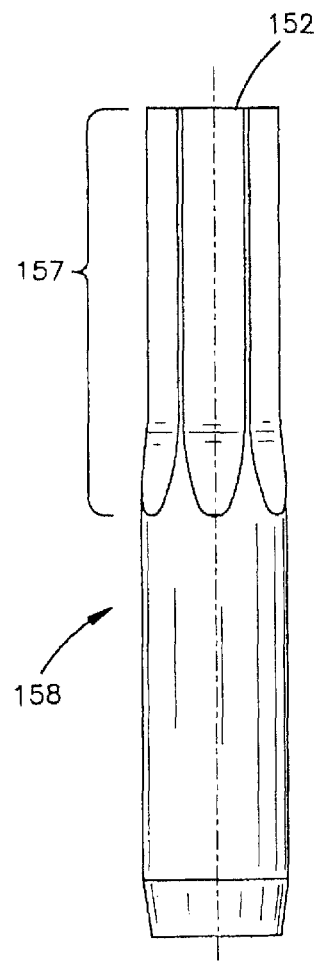
FIG. 10C shows an enlarged side view of the engagement portion of the cannulated screwdriver of FIGS. 10A-10B.
Figure 10D:
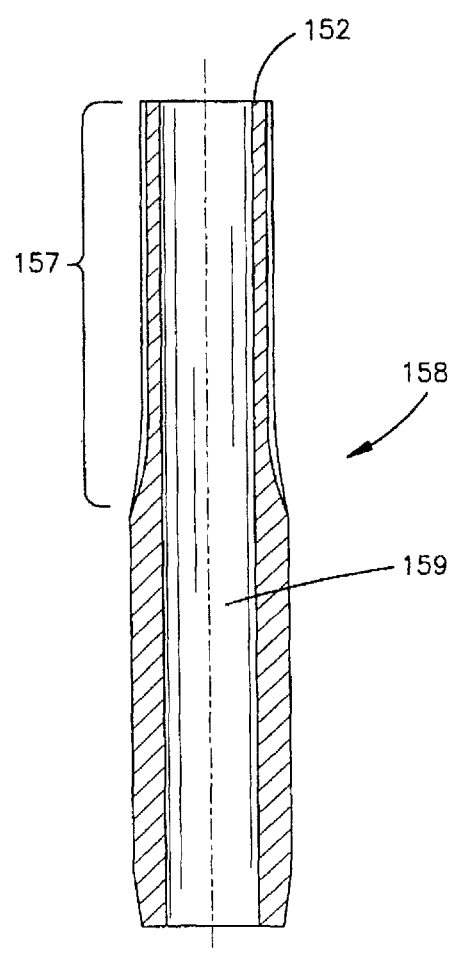
FIG. 10D shows a cross-sectional view of the engagement portion of FIG. 10C.

FIGS. 10A-10D show an embodiment of a cannulated screwdriver 150 for use with the combi-instrument 100. Screwdriver 150 may be substantially similar to screwdrivers 16, 50 described above. Screwdriver 150 may have a leading end 152, a trailing end 154, a bore 156, and a leading portion 158 at and/or near the leading end 152. As seen in FIGS. 10A-10B, screwdriver 150 may be sized to interact with locking collar 115. Leading portion 158 is shown in more detail in FIGS. 10C-10D. Leading portion 158 may have an engaging portion 157 for engaging a bone screw 1. Leading portion 158 may also have a bore 159 coaxial with but of a reduced diameter than bore 156 of screwdriver 150. Leading portion 158 may also be a separate and distinct component of screwdriver 150, and accordingly may be a least partially inserted into bore 156 of screwdriver 150. Any and all of the characteristics of leading portion 158 may also be used with screwdriver 16, 50. Screwdriver 150 may be fixedly attached to handle 110 during use.

Figure 11A:
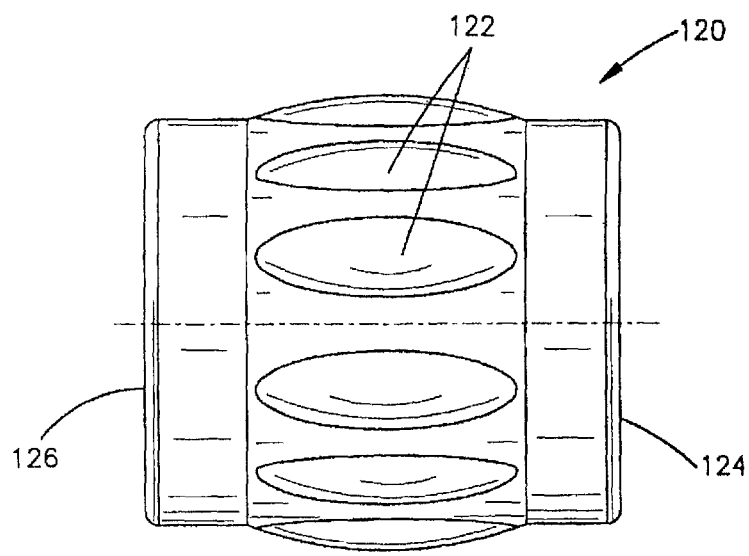
FIG. 11A shows a side view of a locking ring for use with the combi-instrument of FIG. 7A.
Figure 11B:
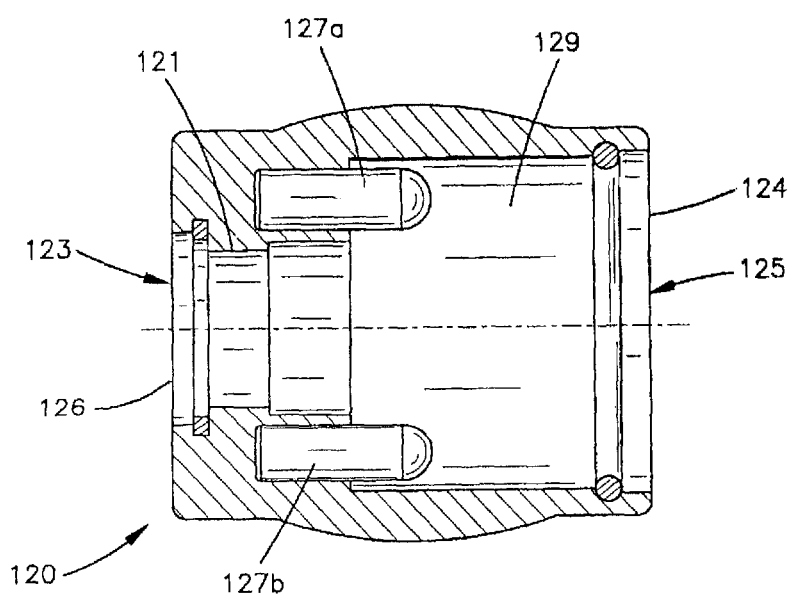
FIG. 11B shows a cross-sectional view of the locking ring of FIG. 11A.

FIGS. 11A-11B show an embodiment of a locking ring 120 for use with combi-instrument 100. As seen in the side view of FIG. 11A and the cross-sectional view of FIG. 11B, locking ring 120 may have indentations 122 to assist gripping, a first end 124, a second end 126, a first opening 125, and a second opening 123. Locking ring 120 may also have locking elements 127a, 127b protruding within the cavity 129 of locking ring 120. Locking elements 127a, 127b may engage indentations 118 of locking collar 115, as discussed below. Locking ring 120 may have one, two, three, or more locking elements. Inner surface 121 of locking ring 120 preferably corresponds to the shape and dimensions of auxiliary shaft portion 139 of compression sleeve 130.

Figure 12A:
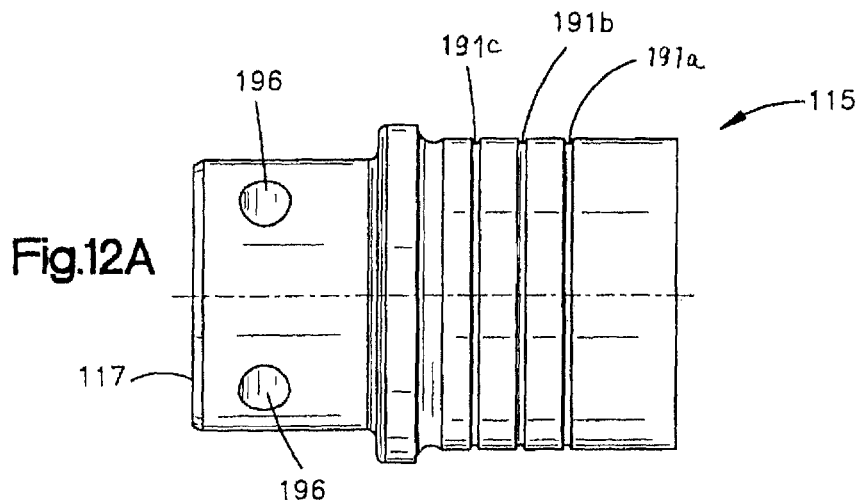
FIG. 12A shows a side view of a locking collar for use with the combi-instrument of FIG. 7A.
Figure 12B:
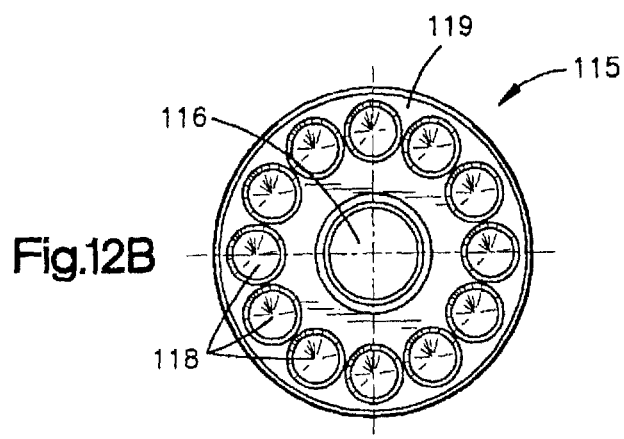
FIG. 12B shows an end view of the locking collar of FIG. 12A.
Figure 12C:
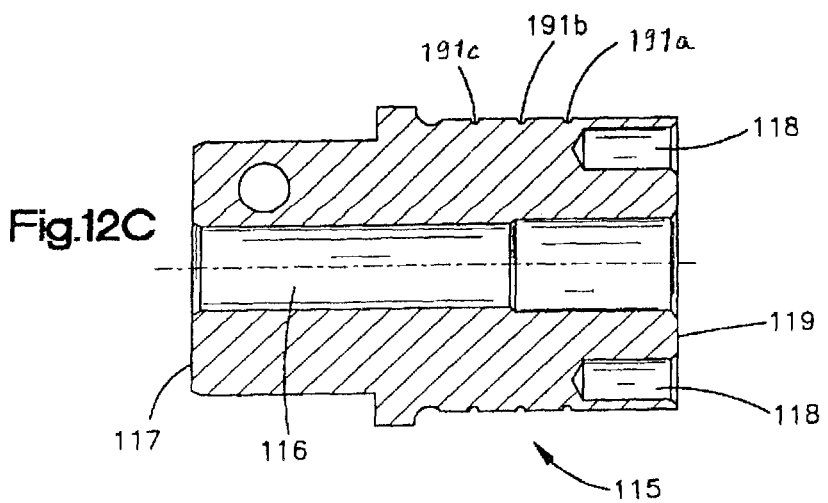
FIG. 12C shows a cross-sectional view of the locking collar of FIG. 12A.

FIGS. 12A-12C show an embodiment of a locking collar 115 for use with combi-instrument 100. As seen in the side view of FIG. 12A, the front view of FIG. 12B, and the cross-sectional view of FIG. 12C, locking collar 115 may have an insertion end 117 for insertion into a handle 110, and an engaging end 119 for engaging a locking ring 120. Locking collar 115 may also have a bore 116 extending between ends 117, 119. As seen in detail in FIG. 12B, the engaging end 119 of locking collar 115 may have a plurality of indentations 118 disposed around bore 116. Some indentations 118 may engage locking elements 127a, 127b of locking ring 120. Locking collar 115 is fixedly attached to handle 110 by way fasteners being inserted into fixation holes 196, which may align with the fixation holes 194 of handle 110. Fixation holes 194, 196 may be threaded.

Locking collar 115 may also have indicia 191a, 191b, 191c, which may be utilized in a substantially similar manner as indicia 56a, 56b, 56c of screwdriver 50 (discussed supra), such that as the insertion of the bone screw 1 in a bone or tissue progresses, indicia 191a, 191b, 191c are progressively covered up. Indicia 56, 191 may be different colors to indicate the level of insertion of bone screw 1. Indicia 56, 191 may be spaced apart as a variety of distances. Indicia 56, 191 are preferably spaced apart at about 2 mm.

The engagement and release of locking collar 115 with locking ring 120 will now be described. After the bone screw 1 is threaded attached to compression sleeve 130 by engaging internal threads 134 with the rear threaded segment 7 of bone screw 1, the combi-instrument 100 is arranged such that the locking elements 127 of the locking ring 120 engage indentations 118 of the locking collar 115. In this configuration, the entire combi-instrument 100 is essentially an integral tool. The combi-instrument 100 is then rotated and/or otherwise manipulated to insert bone screw 1 into a bone or tissue to a desired depth, but preferably such that the leading end 133 of the compression sleeve 130 is near the bone or tissue surface. At this point, the locking ring 120 may be slid toward the distal end of the device, such that locking elements 127 become disengaged with indentations 118 of locking collar 115. Locking ring 120 preferably is slid in this direction to the point that it abuts compression sleeve 130. After locking ring 120 is disengaged, handle 110 (with screwdriver 150 and locking collar 115 fixedly attached) may be rotated to further insert the bone screw 1 into a bone or tissue, while concurrently disengaging the rear threaded segment 7 from the internal threads 134 of the compression sleeve 130. This is achieved because the engaging portion 157 of the screwdriver 150 is now allowed to engage the bone screw 1 and rotate free of the compression sleeve 130 within its bore 131.

FIGS. 13A-14B show another embodiment of a compression sleeve 200 and an embodiment of a plastic seal 220 for use with a bone screw 1, and in accordance with the overall objectives of the invention described herein. As seen in the side view of FIG. 13A, the enlarged side view of FIG. 13B, and partial cross-sectional view of FIG. 13C, compression sleeve 200 may have a bore 202 extending between leading opening 204 and trailing opening 206. Bore 202 may have more than one diameter. Compression sleeve 200 may also have a shaft portion 208, and a tip portion 209 having a leading end 210. As seen in more detail in FIGS. 13B-13C, tip portion 209 may have a hex-shaped inner surface 212 for receiving a portion of a plastic seal 220 (see FIGS. 14A-14B, infra). Inner surface 212 may be other shapes as well suitable for restricting rotational movement of a plastic seat 220 within the tip portion 209. Tip portion 209 may also have a ring 214 disposed near the leading end 210 for elastically securing a portion of a plastic seal 220. Ring 214 may be elastically deformable so as to allow a portion of a plastic seal 220 to engage the ring 214 while still allowing the plastic seal 220 to slide past the ring and further into the bore 202.

Figure 14A:
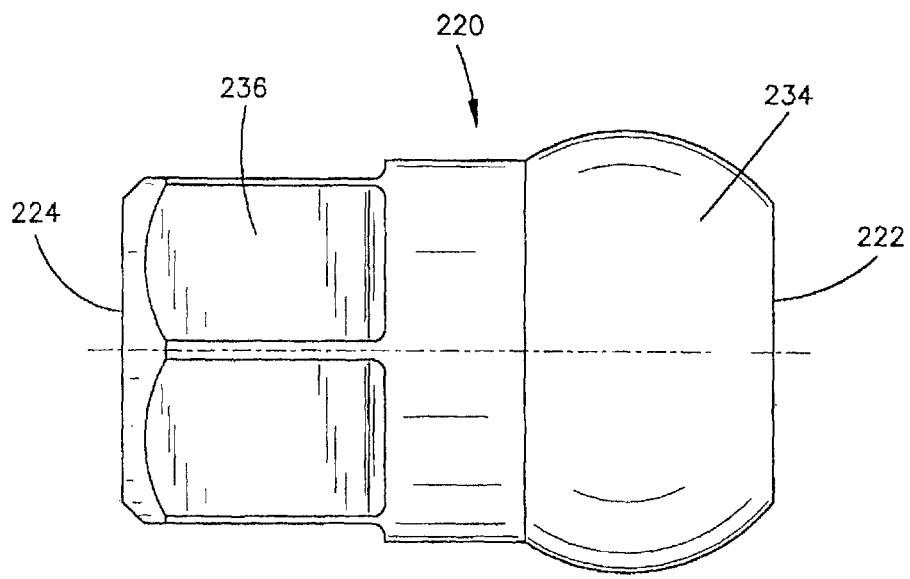
FIG. 14A shows a side view of a plastic seal for use with a screw.
Figure 14B:
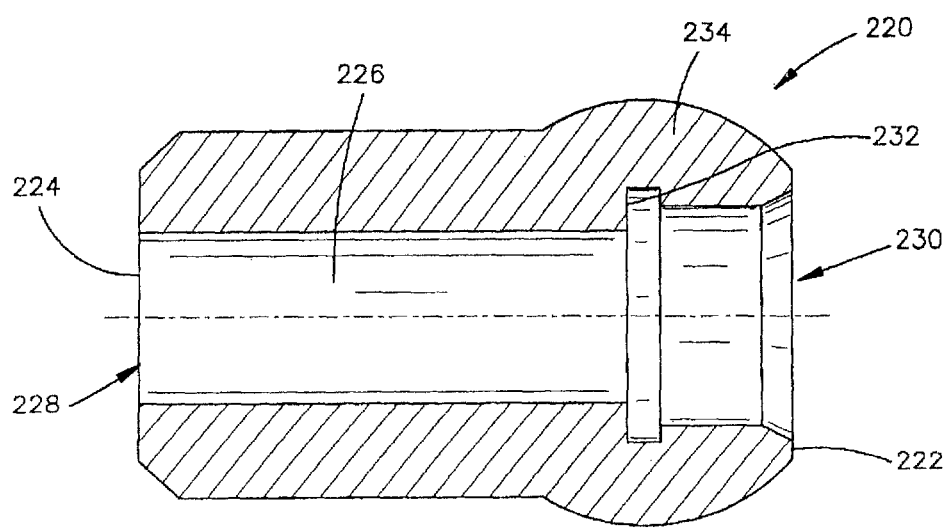
FIG. 14B shows a cross-sectional view of the plastic seal of FIG. 14A.

FIGS. 14A-14B show an embodiment of a plastic seal 220 for use with compression sleeve 200 and bone screw 1. As seen in the side view of FIG. 14A, and the cross-sectional view of FIG. 14B, seal 220 may have a leading end 222, an insertion end 224, with a bore 226 extending between leading opening 230 and trailing opening 228. Seal 220 may also have a bulbous leading portion 234 for receiving a portion of a bone screw 1. The inner surface of the leading portion 234 may have a shoulder 232, similar in design and function to shoulder 22, 46, 136 described above. The inner surface of leading portion 234 may or may not be threaded. In one embodiment, the inner surface is not threaded, and bone screw 1 is inserted into the leading portion 234 by axial force. In another embodiment, inner surface is threaded, and bone screw 1 may be threadedly received within leading portion 234. Seal 220 may also be molded over at least a portion of bone screw 1. Seal 220 may also have a hex-shaped outer surface 236 at or near the insertion end 224, which may be inserted into the hex-shaped inner surface 212 of compression sleeve 200. Other shapes other than hex-shaped surfaces may be utilized. Seal 220 is preferably made of plastic, and is preferably a single-use, disposable element.

In use, bone screw 1 is inserted into the leading opening 230 of seal 220, and the insertion end 224 is inserted within the leading opening 204 of compression sleeve 200, such that the hex-shaped outer surface 236 of the seal 220 engages the hex-shaped inner surface 212 of the compression sleeve 200. Bone screw 1 may then be partially inserted into bone or tissue to a desired depth. Bone screw 1 may then be engaged by a screwdriver via bore 206 of compression sleeve 200 to insert screw 1 further into bone or tissue, and concurrently disengaging bone screw 1 with seal 220. Bone screw 1 may be engaged as such until the bone screw 1 is completely disengaged with seal 220. Plastic seal 220 may then be removed from compression sleeve 200 and discarded.

Bone screw 1 may be fully or partially inserted into instrument 15 or compression sleeve 30, 130, 200 prior to engagement with a bone surface. Threaded portions of bone screw 1 may have a variety of pitches, lengths, diameters, and different threaded segments on a bone screw 1 may have the same or different pitches, lengths, and diameters. Various combinations of characteristics will be appreciated by those skilled in the art.

It is expressly contemplated that characteristics from some embodiments may be combined, integrated, or interchangeable with characteristics from other embodiments. In this sense, the described components of the instruments described herein are "modular" in nature. Such combinations will be appreciated by those skilled in the art, in addition to modifications thereof.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention, and that various modifications may be made by those skilled in the art which will embody the principles of the invention and fall within the spirit and the scope thereof.

The invention claimed is:

1. A method for implanting a bone screw, comprising the steps of:
   screwing into a threaded bore in a distal portion of an implantation instrument a rear threaded portion of a bone screw having a front threaded portion separated from the rear threaded portion by an unthreaded middle portion, the bone screw further including a central bore hole therethrough dimensioned to accommodate a guide wire;
   inserting the guide wire into a first target portion of bone;
   inserting the implantation instrument over the guide wire such that the front threaded portion of the bone screw is adjacent to the first target portion of bone;
   rotating the implantation instrument to insert the front threaded portion of the bone screw into the first target portion of bone while a locking component is engaged to prevent rotation of the bone screw relative to the implantation instrument; and
   rotating the bone screw with a driving tool to drive the bone screw further into the first target portion of bone to a desired depth and out of engagement with the implantation instrument while the locking component is disengaged to permit rotation of the bone screw relative to the implantation instrument.

2. The method of claim 1, further comprising the step of:
   determining the desired depth of insertion for the bone screw into the first target portion of bone based on at least one indicia on the driving tool.

3. The method of claim 2, wherein the driving tool has a plurality of indicia spaced apart from one another.

4. The method of claim 1, wherein the implantation instrument further comprises at least one indicia, and wherein the rotating step further comprises utilizing the at least one indicia to assess the insertion depth of the bone screw.

5. The method of claim 4, wherein the at least one indicia are disposed on a locking collar fixedly attached to the driving tool.

6. The method of claim 1, wherein in the rotating step, first and second segments of first target portion of bone are compressed relative to one another.

7. The method of claim 1, wherein the implantation instrument includes a bore configured to retain the rear threaded portion of the bone screw, the driving tool and the locking component.

8. The method of claim 1, wherein the locking component includes at least one protrusion engageable with a locking collar fixed attached to the driving tool.

9. The method of claim 1, wherein a pitch of the front threaded portion is substantially different than a pitch of the rear threaded portion.

10. The method of claim 1, wherein a pitch of the front threaded portion is substantially equal to a pitch of the rear threaded portion.

11. The method of claim 1, wherein a leading portion of the front threaded portion is substantially different than a leading portion of the rear threaded portion.

12. The method of claim 1, wherein a leading portion of the front threaded portion is substantially equal to a leading portion of the rear threaded portion.

13. The method of claim 1, wherein the locking component is slidably associated with the driving tool.

* * * * *